United States Patent [19]

Bonelli et al.

[11] Patent Number: 4,716,149
[45] Date of Patent: Dec. 29, 1987

[54] PARTIALLY MODIFIED, RETRO-INVERSO NEUROTENSIN ANALOGS

[75] Inventors: Fabio Bonelli; Antonello Pessi, both of Rome; Antonio S. Verdini, Monterotondo, all of Italy

[73] Assignees: Enichem S.p.A.; Eniricerche S.p.A., both of Milan, Italy

[21] Appl. No.: 808,617

[22] Filed: Dec. 13, 1985

[30] Foreign Application Priority Data

Dec. 21, 1984 [IT] Italy ................... 24197 A/84

[51] Int. Cl.$^4$ .................. A61K 37/02; C07K 7/08
[52] U.S. Cl. ................... 514/13; 530/327; 530/328
[58] Field of Search ............. 530/327, 328; 514/13

[56] References Cited

U.S. PATENT DOCUMENTS

| | | | |
|---|---|---|---|
| 3,929,756 | 12/1975 | Leeman et al. | 530/327 |
| 4,110,321 | 8/1978 | Folkers | 530/327 |
| 4,331,661 | 5/1982 | Marki et al. | 530/328 |
| 4,439,359 | 3/1984 | Holly et al. | 530/327 |
| 4,439,360 | 3/1984 | Verdini et al. | 530/330 |
| 4,613,586 | 9/1986 | Barchas et al. | 514/13 |

OTHER PUBLICATIONS

Chem. Abstr., vol. 104, (1986), 103113.

*Primary Examiner*—Delbert R. Phillips
*Attorney, Agent, or Firm*—Hedman, Gibson, Costigan & Hoare

[57] ABSTRACT

Pharmacologically active, partially retro-inverso, neurotensin-like peptides lasting longer than the natural hormone, corresponding to the formula

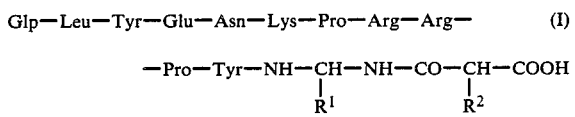

wherein $R^1$ and $R^2$ are straight or branched ($C_1$–$C_7$) alkyl radicals.

The new compounds are useful as vasodilating and hypotensive agents.

7 Claims, No Drawings

PARTIALLY MODIFIED, RETRO-INVERSO NEUROTENSIN ANALOGS

The present invention refers to new, pharmacologically active, partially retro-inverso, neurotensin analogs useful as vasodilating and hypotensive agents. More particularly the present invention relates to neurotensin analogs of general formula (I):

Glp—Leu—Tyr—Glu—Asn—Lys—Pro—Arg—Arg— (I)

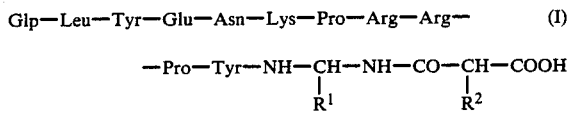

wherein $R^1$ and $R^2$, each independently, represent straight or branched alkyl radicals of from 1 to 7 carbon atoms. According to a preferred embodiment of the present invention, $R^1$ and $R^2$, each independently, are selected from the group consisting of methyl, ethyl, propyl, isopropyl, butyl, isobutyl, t-butyl, pentyl, isopentyl, hexyl, and heptyl. According to a most preferred embodiment of the present invention $R^1$ is

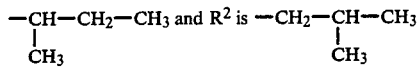

Neurotensin (NT), a natural tridecapeptide of nervous and intestinal origin has multiple effects on the mammalian cardiovascular system.

NT actions affecting the cardiovascular system comprise:

(a) lowering of blood pressure in the rat, rabbit, pig, goat and dog;

(b) change in heart rate;

(c) increase in permeability of blood microvessels and vasodilation in the rat;

(d) positive inotropic and chronotropic effects in the isolated atria in the rat and guinea pig;

(e) vasoconstriction in the adipose tissue in the dog, in the perfused heart and isolated portal vein in the rat;

(f) vasodilation in the dog intestine, (F. Rioux, R. Keronac, R. Quirion and S. St-Pierre, Ann. New York Acad. Sci., 400, 57, (1982) and references cited therein). Although the relative importance and the specific role of these and other possible biological effects elicited by NT remains to be established, particularly in humans, the interaction between NT and the cardiovascular system has necessarily remarkable physiological and/or pathological implications.

First of all, NT is active on the cardiovascular system in a variety of animal models at relatively low dosages (50–1000 μmol); secondly, immunoreactive NT has been demonstrated in the cardiac nerves; furthermore the development of specific NT antagonists has provided evidence to the specific NT receptors in the vascular and cardiac smooth muscle cells. Experiments have shown that NT interacts with structures such as the autonomic nervous system and the mast cells.

NT is also present significantly in the mammalian gastrointestinal tract.

Of particular interest are those studies concerning the stability of NT intact molecules in blood plasma, their metabolic fate and the physiological activity of the fragments obtained by NT enzymatic degradation in vivo.

Preliminary studies on NT metabolism have been carried out in the rat, following an intravenous injection of synthetic NT and either soluble or heterogeneous fractions of rat brain.

It has been found that NT is rapidly hydrolyzed in rats; the most susceptible bonds in NT sequence are $Arg^8$—$Arg^9$ (trypsin-like enzymes) and $Tyr^{11}$—$Ile^{12}$ (convertase-like enzymes), while in the rat brain fractions, the most susceptible bond is $Pro^{10}$—$Tyr^{11}$ (proline endopeptidase-like enzyme). Other sites at which degradation may preferentially occurs are: the $Ile^{1\text{-}2}$—$Leu^{13}$ bond by carboxypeptidases, the $Glp^1$—$Leu^2$ bond by L-pyroglutamyl-hydrolases and the $Tyr^3$—$Glu^4$ bond by chymotrypsin.

Structure-activity studies with various fragments of the hormone showed that the C-terminal 9–13 fragment is the minimal structure required for the full expression of the biological activity of neurotensin (Union Med. Can., 1980, 109(10), 1447-8, 1451-2, 1454-5—Chemical Abstracts 94, 41705t). More particularly, while tyrosine-11 appears to be essential for maintaining the intrinsic activity of the peptide and the sequence $Arg^9$—$Pro^{10}$—$Tyr^{11}$ is responsible for the pharmacological activity on the heart and on the stomach smooth muscle, the isoleucine-12 and leucine-13 residues proved to be very important for binding. Further studies have shown that there is a good agreement between receptor-binding potency of the peptide and its pharmacological effect. NT and NT analogs modified at the leucine-13 group, such as neurotensin—$NH_2$ and ($Gln^4$)—neurotensin—$NH_2$, in fact, showed less than 1% of the neurotensin and ($Gln^4$) neurotensin pharmacological activities respectively (Proc. Natl. Acad. Sci. USA, 1976, 73(11), 3833-7, Chemical Abstracts 86, 50865 g).

We have now surprisingly found that the NT analogs of formula I wherein the direction of the $Ile^{12}$—$Leu^{13}$—CO—NH— bond has been reverted, show an enhanced stability toward enzymatic hydrolysis, when compared with the parent NT molecule, while retaining the biological activity of the natural peptide. Like NT, the retro-inverso peptides of the present invention in fact showed to be able to induce a characteristic vasodilation visible on the rat skin after intravenous injection (S. E. Leeman and R. E. Carraway, Ann. New York Acad. Sci., 400, 1, (1982) and references cited therein).

The reversal of the direction of the peptide bond which is carried out according to the general methods described in Italian patent application Nos. 25755 A/81, 20926 A/82 and 23417 A/82 and Nos. EP-B-82568 and EP-A-97994 yields structural isomers of the reference peptide wherein the $Ile^{12}$—$Leu^{13}$—CONH— bond is more resistant toward carboxypeptidase action.

This reversal also enhances the stability of the $Tyr^{11}$—$Ile^{12}$ bond because of an induced long-distance conformational change effect thus rendering the whole molecule more stable to proteolytic degradation.

In particular, according to the present invention, the reversal of the $Ile^{12}$—$Leu^{13}$ peptide bond is accomplished through conversion of Ile into the corresponding geminal diamino residue

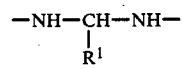

wherein $R^1$ is as defined above and conversion of Leu into the corresponding 2-substituted-malonyl residue

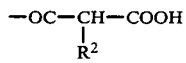

wherein $R^2$ is as defined above.

The incorporation of the fragment

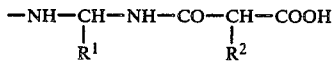

into the NT peptide chain may be achieved by solid-phase synthesis.

Residue (II) is incorporated following coupling of the 2-alkyl-malonyl-D-isoleucinamide precursors to an insoluble polyacrylamide matrix and subsequent conversion of the primary amides to amines by (1,1-bis-(trifluoroacetoxy)iodo)benzene (TIB), as described in Nos. EP-A-97994 and EP-A-127234.

The synthesis is then brought to completion according to the usual method employed in the solid-phase synthesis of peptides which consists in assembling the desired peptide sequence by the sequential addition of the individual amino acids to the suitably selected polymer matrix to which the peptide is attached up to completion of the synthesis. Once the sequence has been assembled, the peptide is recovered by treatment with a suitable reactant which detaches it from the resin.

The polymer which is preferably used in the synthesis of the present invention consists in beads of a polyamide resin appropriately functionalized with substituted benzyl alcohol residues (R. Arshady et al., J. Chem. Soc. Perkin I, 529 (1981)).

2-Alkyl-malonyl-D-isoleucinamide precursors are then attached to these residues through ester bond formation preceded by activation of the free carboxylic groups in suitable conditions.

The substituted benzyl alcohol residue linking the growing peptide to the insoluble resin allows, at the end of the synthesis, detachment of the desired peptide from the resin and simultaneous cleavage of all the protecting groups of the amino acid side chain functional groups upon treatment with a 6% solution of thioanisole in trifluoroacetic acid.

The above general method affords a compound of formula I wherein all the aminoacids have the L-configuration, the asymmetric carbon atom of the gem-diammino residue

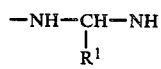

has the same configuration as L-phenylalanine, while the asymmetric carbon of the malonyl residue

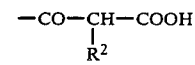

may have the R- or S-configuration. If separation of the thus obtained mixture of diastereoisomers into the single isomers is desired, this can be easily accomplished by known methods such as for instance, preparative HPLC on carboxylmethylcellulose supports.

The example below illustrates in detail the preparation of a representative compound of the present invention.

The following abbreviations have been used throughout the specification:

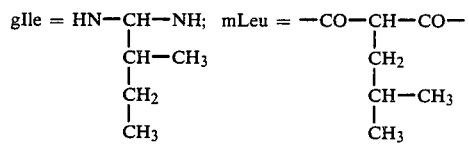

DMF=dimethylformamide; DCC=dicyclohexylcarbodiimide; NMM=N-methylmorpholine; DIPEA=-diisopropylethylamine; TFA=trifluoroacetic acid; OTCP=Trichlorophenyl ester; ONP=4-nitrophenyl ester; OPCP=pentachlorophenyl ester; THF=tetrahydrofuran; EtOAc=ethyl acetate; Fmoc=9-fluorenylmethyloxycarbonyl; Boc=t-butoxycarbonyl; Mtr=4-methoxy-2,5,6-trimethylsulphonyl; HOBt=N-hydroxy benzotriazole.

EXAMPLE

Preparation of the peptide

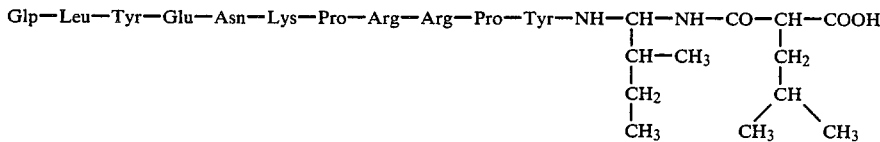

The synthesis is carried out by the solid-phase method, in a modified Beckman 990 Peptide Synthetizer, according to the methodology described in Nos. EP-A-97994 and EP-A-127234 and Pessi A., Pinori M., Verdini A. S. and Viscomi G. C., J. Chem. Soc. Chem. Commun., 195, (1983). The polyamide resin (containing 1.0 meq of sarcosine per gram of resin) is activated by treatment with ethylenediamine (16 h, 20° C.) and then functionalized with (Fmoc—Nle)$_2$O and with

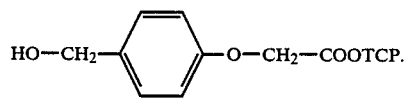

This last compound which represents the acid-labile linkage agent between the resin and the peptide to be assembled, is esterified on the resin with the HO—m-Leu—D—Ile—NH$_2$ residue, after activation of the malonyl carboxyl group.

HO—mLeu—D—Ile—NH$_2$ is synthesized independently through condensation of HCl.D—Ile—NH$_2$ with the emiester mLeu—(OEt)—OH via steps A and B.

(A) Synthesis of HCl.D—Ile—NH$_2$

Boc—D—Ile—OH (27.48 mmol) is dissolved in THF (60 ml); the solution is cooled to −15° C., and, sequentially, NMM (27.48 mmol), isobutylchloroformate (27.48 mmol) and, 3 minutes later, 30% NH4OH (42.80 mmol) are slowly added thereto while keeping the temperature ≦10° C. After 30 minutes at −15° C. and 60 minutes at +20° C., the reaction mixture is diluted with H2O to a 1000-ml volume; the product is recovered by filtration and dried under vacuum for 16 hours.

Cleavage of Boc protecting group is achieved by treatment with 4.8M HCl in EtOAc for 180 minutes.

Yield: 15.12 mmol (53%) M.p. 247°–48° C. (lit. 246°–47° C.).

$[\alpha]_D^{20} = -21.88°$ (c=1 in H2O) (lit. −21.0°).

(B) Synthesis of HO—mLeu—D—Ile—NH2 mLeu(OEt)OH (7.2 mmol) is dissolved in CH2Cl2 and the obtained solution is cooled to 0° C. HOBt (7.92 mmol) dissolved in DMF (1 ml) and DCC (7.92 mmol) are added thereto.

The mixture is stirred for 30 minutes at 0° C. and for additional 30 minutes at +20° C., then it is filtered directly into a solution of D—Ile—NH2 (3 mmol) and NMM (3.6 mmol) in DMF.

The mixture is stirred for 12 hours at 20° C.; after removal of the solvents under vacuum, the residue is taken up in EtOAc and washed with 5% NaHCO3, 0.1M HCl and saturated aqueous NaCl solution, then dried over MgSO4. After filtration and removal of the solvent under vacuum, the residue is crystallized from EtOAc/petroleum ether.

EtO—mLeu—D—Ile—NH2 is dissolved in dioxane/H2O (4/1) and 1M NaOH (2 eq) in dioxane/H2O (1/1) is added thereto.

After 30 minutes at 20° C., dioxane is evaporated off under vacuum and the aqueous phase is extracted with EtOAc, acidified with concentrated HCl up to pH 2, then extracted again with EtOAc; this last organic phase is washed with H2O up to neutral reaction and dried over MgSO4.

After filtration and removal of the solvent under vacuum, the oily residue is taken up in dioxane and freeze-dried.

Yield: 1.69 mmol (56%). M.p. 144°–47° C. The assigned structure has been confirmed by mass spectrometry and 1H-NMR.

HO—mLeu—D—Ile—NH2 is dissolved in CH2Cl2 and activated for 30 minutes at 0° C. with HOBt (1 eq) and DCC (1 eq); the solution is filtered directly into the resin containing reaction vessel and NMM (1 eq) and DMAP (1 eq) are added thereto.

The reaction is allowed to proceed for 16 hours at 20° C.

The resin-bound peptide is then treated with TIB in the reaction conditions already described; after neutralization of trifluoroacetic acid with DIPEA, acylation with ((Fmoc—Tyr—(Bu$^t$))2O is carried out, followed, sequentially, by acylation with (Fmoc—Pro)2O, ((Fmoc—Arg(Mtr))2O, ((Fmoc—Arg(Mtr))2O, (Fmoc—Pro)2O, ((Fmoc—Lys(Boc))2O, Fmoc—Asn—OPCP (with 1 equivalent of HOBt), ((Fmoc—Glu(Bu$^t$))2O, ((Fmoc—Tyr(Bu$^t$))2O, (Fmoc—Leu)2O, Glp—OPCP (with 1 equivalent of HOBt), according to standard cycles of acylation—washing—cleavage of the Fmoc protecting group of the N-terminal amino acid.

Aminoacid analysis of the end peptide/resin is the following: Ile, 1.63; Leu 1.01; Arg, 1.89; Lys, 0.97; Pro, 2.00; Asn, 0.96; Glu, 2.06; Tyr 1.71.

Detachment of the tridecapeptide from the resin is accomplished by treatment with 90% TFA for 210 minutes at +20° C.; after filtration, the reaction solvents are removed under vacuum and the residue is freeze-dried.

Amino acid analysis for ((Arg$^8$(Mtr),Arg$^9$(Mtr),gIle$^{12}$,(R,S)—mLeu$^{13}$))NT is the following: Leu, 1.00; Arg, 2.11; Lys, 1.01; Pro, 2.13; Asn, 1.02; Glu, 2.25; Tyr, 1.99.

After purification of the tridecapeptide wherein the arginine moieties are protected, through ion-exchange chromatography (Whatman DEAE 52 resin, linear gradient of 0.01–0.3M NH4HCO3, pH 8.6), the peptide is treated with a 6% solution of thioanisole in TFA for 5 hours at +20° C.; after removal of the solvents, the residue is freeze-dried. The end peptide ((gIle$^{12}$,(R,S)—mLeu$^{13}$))—NT is purified through ion-exchange chromatography (Whatman CM-52 resin, linear gradient of 0.03–0.3M NH4OAC, pH 6.6). The purified peptide shows single spots on HPLC chromatography (column Novapack C-10 (5 μm), eluting with CH3CN/0.01M NH4OAc pH 7.0) and thin-layer chromatography and the correct amino acid analysis: Leu, 1.00; Arg, 2.08; Lys, 1.06; Pro, 1.95; Asn, 1.04; Glu, 2.08; Tyr, 1.99.

We claim:

1. A neurotensin-like peptide, partially retro-inverted at the Ile—Leu bond, of the general formula (I):

Glp—Leu—Tyr—Glu—Asn—Lys—Pro—Arg—Arg—    (I)

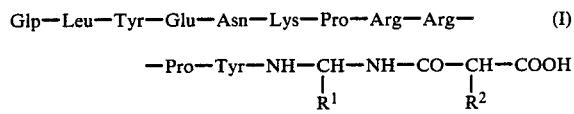

wherein R$^1$ and R$^2$ are straight or branched alkyl radicals of from 1 to 7 carbon atoms.

2. A peptide as in claim 1 wherein R$^1$ and R$^2$, each independently, are selected from methyl, ethyl, propyl, isopropyl, butyl, isobutyl, t-butyl, pentyl, isopentyl, hexyl, and heptyl.

3. A peptide as in claim 2 wherein R$^1$ is

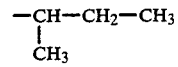

and R$^2$ is —CH2—CH(CH3)2.

4. A peptide as in claims 1, 2 or 3 characterized in that the gem-diamino residue

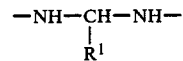

has the S-configuration and the malonyl residue

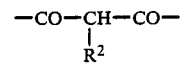

is a mixture of the R- and S-enantiomers.

5. A peptide as in claims 1, 2 or 3 wherein the gem-diamino residue has the S-configuration and the malonyl residue has the S configuration.

6. A peptide as in claims 1, 2 or 3 wherein the gem-diamino residue has the S configuration and the malonyl residue has the R configuration.

7. A method of generating a vasodilating and hypotensive effect in a warm-blooded animal comprising administering to said warm-blooded animal a vasodilating and hypotensive effective amount of the neurotensin-like peptide of claim 1.

* * * * *